United States Patent [19]

Haag et al.

[11] 4,358,395

[45] Nov. 9, 1982

[54] HYDROGEN REGENERATION OF COKE-SELECTIVATED CRYSTALLINE ALUMINOSILICATE CATALYST

[75] Inventors: Werner O. Haag, Lawrenceville; David H. Olson, Pennington; Paul G. Rodewald, Rocky Hill, all of N.J.

[73] Assignee: Mobil Oil Corporation, New York, N.Y.

[21] Appl. No.: 941,606

[22] Filed: Sep. 11, 1978

[51] Int. Cl.³ .................. B01J 29/38; C07C 1/24; C07C 2/66; C07C 5/22
[52] U.S. Cl. ........................ 252/411 R; 585/408; 585/466; 585/467; 585/469; 585/640
[58] Field of Search ............ 252/411 R; 260/668 R, 260/668 A, 671 R, 671 C, 681–682; 585/408, 469, 640, 467, 466

[56] References Cited

U.S. PATENT DOCUMENTS

| 4,001,346 | 1/1977 | Chu | 260/671 C |
| 4,088,706 | 5/1978 | Keading | 260/681 |
| 4,128,592 | 12/1978 | Keading | 260/671 R |

Primary Examiner—P. E. Konopka

Attorney, Agent, or Firm—Charles A. Huggett; Michael G. Gilman; Malcolm D. Keen

[57] ABSTRACT

A method is provided for regeneration of a catalyst comprising a crystalline aluminosilicate zeolite characterized by a silica to alumina mole ratio of at least about 12, a constraint index, as hereinafter defined, within the approximate range of 1 to 12, which catalyst has undergone controlled precoking by exposing the same to a thermally decomposable organic compound at a temperature in excess of the decomposition temperature of said compound but less than about 1200° F., at a hydrogen to organic compound mole ratio of between 0 and 1 to deposit at least about 1 weight percent coke thereon, such precoked catalyst having been deactivated by formation of a carbonaceous deposit thereon as a result of use of the same in catalytically converting an organic charge under conditions less severe, i.e., at a lower temperature and/or a higher hydrogen concentration than those employed during said precoking which comprises contacting the aged catalyst with an atmosphere comprising hydrogen at a temperature between about 800° F. and about 1200° F. and a pressure between about 0 and about 2000 psig for a period of time sufficient to at least partially restore the activity of the catalyst.

9 Claims, 2 Drawing Figures

HYDROGEN REGENERATION OF COKE-SELECTIVATED CRYSTALLINE ALUMINOSILICATE CATALYST

BACKGROUND OF THE INVENTION

1. Field of the Invention

This invention relates to a method for regeneration of an aged coke-selectivated crystalline aluminosilicate zeolite catalyst by treatment with hydrogen under particular conditions.

2. Description of the Prior Art

It has heretofore been known to employ coke-selectivated catalysts comprising a crystalline aluminosilicate zeolite having a silica to alumina mole ratio of at least about 12 and a constraint index between about 1 and about 12 for conversion of various organic compounds involving reactions such as alkylation, disproportionation, isomerization, cracking, polymerization, aromatization, etc. These catalysts have been found to be particularly useful in selective processes, such as selective toluene disproportionation and aromatics alkylation with olefins. The coke-selectivated catalysts so employed slowly deactivate with time on stream ultimately making regeneration thereof necessary.

Regeneration has heretofore been carried out by contacting the aged catalyst at an elevated temperature with an oxygen-containing atmosphere, e.g., air, to effect removal of coke therefrom. Such procedure has served to restore the initial activity of the catalyst but has resulted in very substantial reduction in selectivity of the catalyst, approaching that of the unselectivated zeolite. Thus, after air regeneration, the catalyst has required reselectivation, i.e., controlled precoking, to restore the desired initial selectivity.

SUMMARY OF THE INVENTION

In accordance with the present invention, it has been discovered that a coke selectivated catalyst comprising a crystalline aluminosilicate zeolite characterized by a silica to alumina mole ratio of at least about 12 and a constraint index within the approximate range of 1 to 12 after use in catalytic conversion under conditions which effect undesirable deposition of a carbonaceous deposit thereon with consequent loss in activity can be regenerated in a hydrogen-rich atmosphere to substantially restore initial activity and selectivity.

It has been found that the activity-reducing carbonaceous deposit laid down during the processing operation can be removed by exposure to hydrogen under specified conditions whereas the selectivity-enhancing coke deposited during controlled precoking is not removed.

Hydrogen regeneration is accomplished by flowing hydrogen or a hydrogen-rich gas over the aged deactivated catalyst. Regeneration is effectively carried out at a temperature between about 800° and about 1200° F. and a pressure within the range of about 0 to about 2000 psig.

DESCRIPTION OF SPECIFIC EMBODIMENTS

Figure 1:
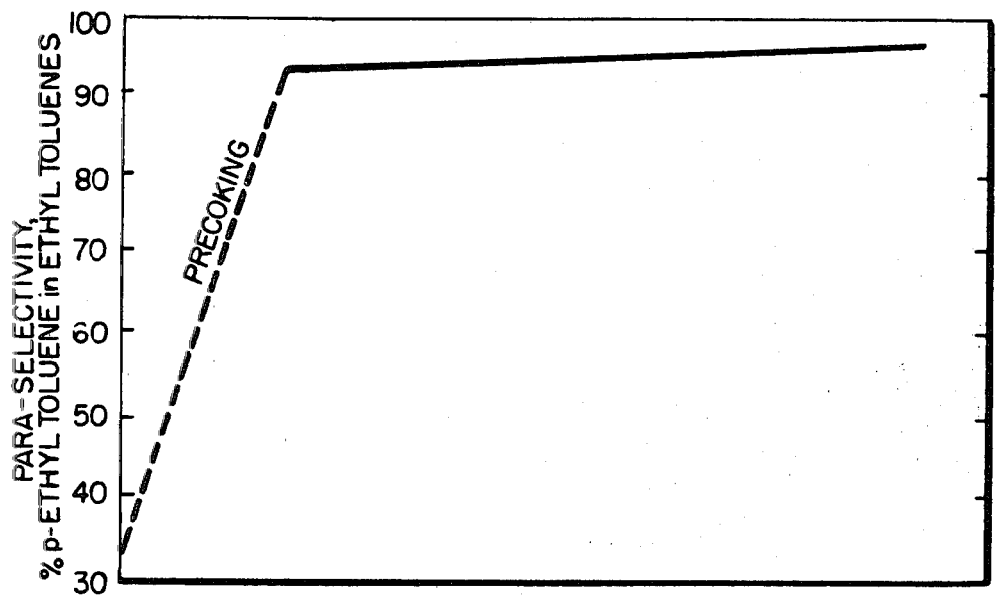
FIG. 1 of the drawing depicts selectivity for para ethyltoluene and conversion of toluene with time on stream during alkylation of toluene with ethylene over a coke-selectivated crystalline aluminosilicate zeolite catalyst of the type used in the present invention.
Figure 1:
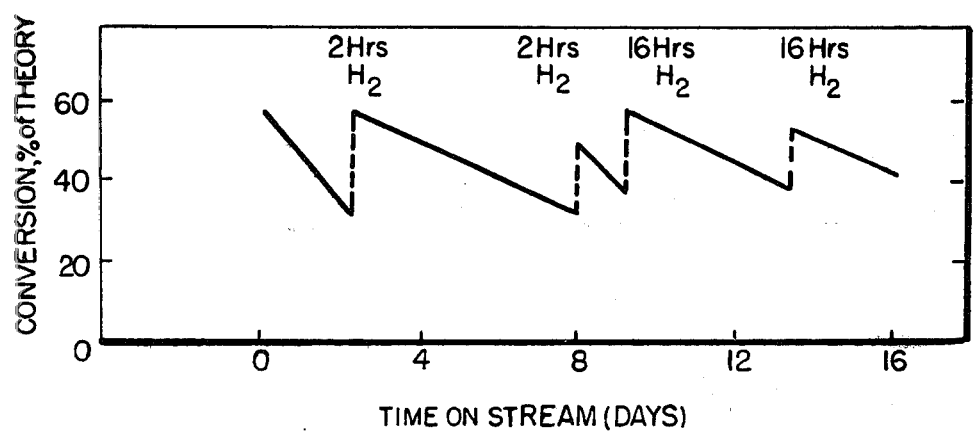

The catalyst undergoing regeneration in accordance with the method described herein comprises a crystalline aluminosilicate zeolite which is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecule of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herin is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cation in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite epistilbite, heulandite, and clinoptilolite. The preferred crystalline aluminosilicates are ZSM-5, ZSM-11, ZSM-12, ZSM-38 and ZSM-35 with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The crystal size of the synthesized zeolite is generally within the approximate range of 0.01 to 40 microns. Preferably, the crystal size of the above-described crystalline aluminosilicate zeolite employed in the conversion and regeneration process of the invention is greater than about 0.5 micron, usually in the approximate range of 1-20 microns and particularly in the range of 1-6 microns. With the use of crystals within such size range, distinctly higher selectivity for production of desired product has been observed as compared with comparable use of smaller size crystals.

When synthesized in the alkali metal form, the zeolite is conveniently converted to the hydrogen form, generally by intermediate formation of the ammonium form as a result of ammonium ion exchange and calcination of ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

Generally, however, the zeolite either directly or via initial ammonium exchange followed by calcination, is preferably hydrogen exchanged such that a predominate proportion of its exchangeable cations are hydrogen ions. In general, it is contemplated that more than 50 percent and preferably more than 75 percent of the cationic sites of the crystalline aluminosilicate zeolite will be occupied by hydrogen ions.

In practicing the desired conversion and regneration process, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families includes the sub-bentonites and the kaolins commonly known as Dixie, McNamee-Georgia and Florida clays or others in which the main mineral constituent is halloysite, kaolinite, dickite, nacrite or anauxite. Such clays can be used in a raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The crystalline aluminosilicate zeolite catalysts employed are coke selectivated prior to use by exposing the catalyst to a thermally decomposable organic compound, e.g., toluene, under high severity conditions at a temperature in excess of the decomposition temperature of said compound, generally greater than 1000° F., but less than about 1200° F., at a hydrogen to organic compound mole ratio between 0 and 1 to deposit the desired quantity of coke thereon, generally an amount of at least about 1 percent by weight.

For toluene and organic compounds of similar reactivity, the temperature employed is greater than 1000° F. With organic compounds that are more readily decomposable than toluene, precoking can be carried out at temperatures of less than 1000° F. With the use of higher temperatures in the aforenoted range, the presence of hydrogen has not been found necessary. With temperatures of less than about 1100° F., preferably some hydrogen, generally at least 0.2 mole of hydrogen per mole of organic compound is desirable.

Organic materials, thermally decomposable under the above temperature conditions to provide coke deposition, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Generally, coke selectivation will be accomplished with a hydrocarbon. The reactivity of hydrocarbons with respect to coke producing decreases in the order: (1) dienes, (2) monoolefins, (3) paraffins and (4) aromatics. Usually, it is contemplated that a thermally decomposable organic compound will be used as the source of coke, which compound is the same as that subsequently undergoing conversion with the pre-coked catalyst. For example, in disproportionation of toluene, an alkyl-substituted aromatic, will be the source of coke and most preferably toluene. In the latter case, toluene is initially brought into contact under conditions of temperature and hydrogen concentration amenable to rapid coke formation.

The amount of coke deposited on the catalyst, prior to conducting conversion therewith, will ordinarily be at least about 1 weight percent. Generally, the amount of coke deposited will not exceed about 60 weight percent. The optimum amount of coke employed will depend among other variables on the crystal size of the aluminosilicate zeolite used and the nature of the catalyst binder, if any, employed.

While it is contemplated that the process described herein may involve use of a crystalline aluminosilicate zeolite of any crystal size, it is preferred that the zeolite crystal size be greater than about 0.5 micron, more preferably in the approximate range of 1 to 20 microns and particularly 1 to 6 microns. It has been found that as a general rule, the smaller the zeolite crystal size, the greater the amount of coke deposition required to achieve comparable results. Thus, on a binder-free basis, it has been observed that with the use of small zeolite crystals, e.g., in the range of 0.02 to 0.05 micron size, greater than 20 weight percent of coke deposition was required to obtain results comparable to those obtained with larger zeolite crystals, e.g., in the range of 1 to 2 microns, having approximately 4 weight percent of coke deposited thereon.

The amount and nature of the binder composited with the crystalline aluminosilicate zeolite also has been found to have a marked effect on the amount of coke deposition required to obtain the desired selectivity characteristics. Thus, while binder-free zeolite of 1 to 2 micron size afforded high paraxylene selectivity with about 4 weight percent of coke deposited thereon, comparable use of a composite of such zeolite (65 percent) and alumina (35 percent) required an average of about 22 weight percent of coke deposition. With the use of small zeolite cyrstals (0.02 to 0.05 micron) and alumina binder (35 percent), it is contemplated that 40 percent or more coke deposition would be required to obtain the desired high paraxylene selectivity. Also, increase in alumina content of the zeolite composite, which desirably is in the form of an extrudate, would be expected to require increased coke deposition to obtain comparable high selectivity. With the use of other binders, such as clay or silica, it is anticipated that the amount of coke required for comparable results may be somewhat less than in the case where alumina is the sole binding material.

The precoked crystalline aluminosilicate zeolites employed in the process described herein are further desirably characterized by certain hydrocarbon sorption capacities and rates. Measurements of such properties are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time, of at least 1 gram per 100 grams of zeolite measured at 120° C. and a xylene pressure of 4.5±0.8 mm of mercury and an ortho-xylene sorption time for 30 percent of said capacity of greater than 100 minutes (at the same conditions of temperature and pressure) are required in order to achieve the desired selective production of para-xylene.

It has been found that zeolites exhibiting very high selectivity for para-xylene production require a very long time up to and exceeding a thousand minutes to sorb o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

| Percent of sorption capacity | Factor (F) to Estimate 30% Sorption Time |
| --- | --- |
| 5 | 36 |
| 10 | 9 |
| 20 | 2.2 |

The coke-selectivated catalyst may, if desired, be modified prior to conversion use by the combination therewith of a minor amount, generally in the range of about 0.5 to about 40 weight percent of a difficulty reducible oxide, such as the oxides of silicon, magnesium, phosphorus, antimony, boron or combination thereof. Modification of the zeolite with the desired oxide or oxides can take place either after or before coke selectivation and generally the latter such modification can readily be effected by contacting the zeolite with a solution of an appropriate compound of the element to be introduced, followed by drying and calcining to convert the compound to its oxide form. The addition to or otherwise combination with the zeolite employed in the present catalyst of a Group VIII metal, such as nickel, is to be avoided. Thus, while hydrogen regeneration of an aged precoked nickel-containing HZSM-5 catalyst served to restore the initial activity, the selectivity thereof was substantially reduced as a result of the hydrogen treatment.

An additional optional treatment which may be carried out either before or after precoking of the catalyst involves a contact with steam. Steaming, when employed, is effectively conducted using an atmosphere containing from about 5 to about 100 percent steam at a temperature of from about 250 to about 1000° C. for a period of between about 0.5 and about 100 hours under pressures ranging rrom sub-atmospheric to several hundred atmospheres.

The regeneration method of the present invention, as aforenoted, has the advantage over the prior employed techniques wherein substantially all coke was removed from the aged catalyst by burning in an oxygen-containing atmosphere in that prior selectivation by coking is generally unnecessary.

The organic compound conversion in which the above described crystalline aluminosilicate zeolite catalysts are employed, prior to regeneration, include those reactions wherein a carbonaceous deposit is inherently laid down on the catalyst as a consequence of the conversion taking place. Typical conversion processes, given by way of example, include the methylation of toluene described in U.S. Pat. Nos. 3,965,207; 3,965,208;

3,965,209; 3,965,210; 4,001,346; 4,002,697 and 4,002,698; disproportionation of toluene to produce benzene and xylenes rich in the para isomer described in U.S. Pat. Nos. 4,011,276; 4,016,219 and 4,097,543; isomerization of xylenes described in U.S. Pat. No. 3,856,872; hydrocarbon conversion described in U.S. Pat. No. 3,790,471; alkylation of aromatic hydrocarbons with olefins described in U.S. Pat. Nos. 3,751,504; 3,751,506; 3,755,483; 3,962,364 and 4,016,218; conversion of lower monohydric alcohols and their ethers, such as methanol and dimethyl ether to hydrocarbon mixtures rich in olefins described in U.S. Pat. Nos. 3,911,041 and 3,979,472; alkylation of olefins described in U.S. Pat. No. 3,906,054; ethylation of toluene or ethylbenzene to selectively produce the para ethyl derivative thereof described in U.S. Pat. No. 4,086,287 and selective production of para dialkyl substituted benzenes described in application Ser. No. 841,073, filed Oct. 11, 1977 and issued as U.S. Pat. No. 4,117,026.

In accordance with the regeneration method of the present invention, the aged catalyst resulting from use in catalyzing an organic compound conversion of the type indicated hereinabove and containing carbonaceous deposit as a result of such conversion in an amount generally between about 0.5 and about 20 weight percent, is exposed to an atmosphere rich in hydrogen. While the presence of inert gases, e.g., nitrogen, methane, carbon monoxide and carbon dioxide may be tolerated, it is generally preferred that the regeneration atmosphere consist essentially of hydrogen. Suitable sources of hydrogen useful for regeneration include synthesis gas and refinery streams such as reformer or hydrocracker effluent. The regeneration conditions are important to the success of the operation. Generally, a temperature between about 800° and about 1200° F. and preferably between about 900° and about 1100° F. will be employed, with the pressure being between about 0 and about 2000 psig and preferably between about 100 and 1000 psig. The use of higher temperatures and pressures within the aforenoted ranges lead to faster regeneration rates.

It is of interest to note that any coke which was deposited during the selectivation procedure, to obtain a catalyst which provides higher selectivities, for example, to a para oriented product, is essentially not removed by the hydrogen regeneration treatment described herein. Without being limited by any theory, it appears that the carbonaceous deposit formed during various conversions of organic compounds such as alkylation, disproportionation, isomerization, cracking, oligomerization, aromatization, etc. has different properties from the coke deposited during selectivation. It is believed that the carbonaceous deposit has a higher hydrogen to carbon ratio and a lower molecular weight than the coke deposited during selectivation. The latter appears to form predominately on the surface of the zeolite crystal whereas the carbonaceous deposit appears to be intracrystalline. It is the carbonaceous deposit which is selectively removed by hydrogen treatment under the conditions specified, essentially restoring the initial catalyst activity while maintaining the desired high selectivity. Such is not possible when oxygen-containing gases are used in which instance all of the coke is removed indiscriminately.

The following examples will serve to illustrate the process of the invention without limiting the same.

EXAMPLE 1

A sample of HZSM-5 (2.0 grams), characterized by a crystal size of 1-2 microns, in the form of an extrudate with 35 weight percent alumina, was selectivated with coke. Selectivation conditions included passing a stream of toluene and hydrogen over the zeolite for 25 hours at 1100° F., 6.5 WHSV, 0.5 $H_2$/toluene and 30 psig.

EXAMPLE 2

The selectivated catalyst of Example 1 was tested for toluene disproportionation by passing a stream of toluene thereover at WHSV of 6.5, a pressure of 400 psig and a hydrogen/hydrocarbon ratio of 4 at a temperature of 900° F. At 17 percent conversion, the paraxylene content of the total exlenes produced was 75 percent.

EXAMPLE 3

The catalyst used in Example 2 was then tested for ethylation of toluene by contacting with a toluene/ethylene/hydrogen stream at a weight hourly space velocity of 28/1.1/0.24, a temperature of 797° F. and a pressure of 100 psig. At a toluene conversion of 55 percent of theory, there was observed 90 percent of para-ethyltoluene in the ethyltoluenes produced. Toluene conversion dropped to 30 percent after two days on stream.

EXAMPLE 4

The catalyst used in Example 3 was then regenerated by treating with hydrogen at a rate of 100cc of hydrogen per minute for 2 hours at 1000° F. It was found that the catalyst could be restored to its initial activity and selectivity.

The catalyst then aged during the next six days to 30 percent conversion. A two hour regeneration by treatment with hydrogen under the above conditions did not completely restore the initial catalyst activity. However, increasing the regeneration time to 16 hours restored the activity as did a subsequent 16 hour regeneration. The selectivity to para-ethyltoluene gradually increased from 90 to 93 percent during the 16 days on stream and was not affected by the hydrogen regeneration.

The above results employing hydrogen regeneration are shown graphically in FIG. 1.

EXAMPLE 5

A sample of HZSM-5 (1.0 g), characterized by a crystal size of 1-2 microns, in the form of an extrudate with 35 weight percent alumina, was selectivated with coke. Selectivation conditions included passing a stream of toluene over the extrudate particles for 112 hours at 1050° F., 6.5 WHSV, 0.5 $H_2$/HC and 30 psig.

EXAMPLE 6

The selectivated catalyst of Example 5 was used for toluene disproportionation for six months by passing a stream of toluene thereover at a WHSV of 6.5, $H_2$/HC=4, and a pressure of 400 psig. During this period, catalyst aging was compensated by increasing the temperature from 900° F. at the beginning to 905° F. at the end of the cycle. The toluene conversion was 24 percent. The para-xylene content of the total xylenes produced was 82 percent at the beginning and 93 percent at the end of the six month period. For comparison, the catalyst prior to coke selectivation gave xylenes containing only 30% p-xylene.

EXAMPLE 7

Figure 2:
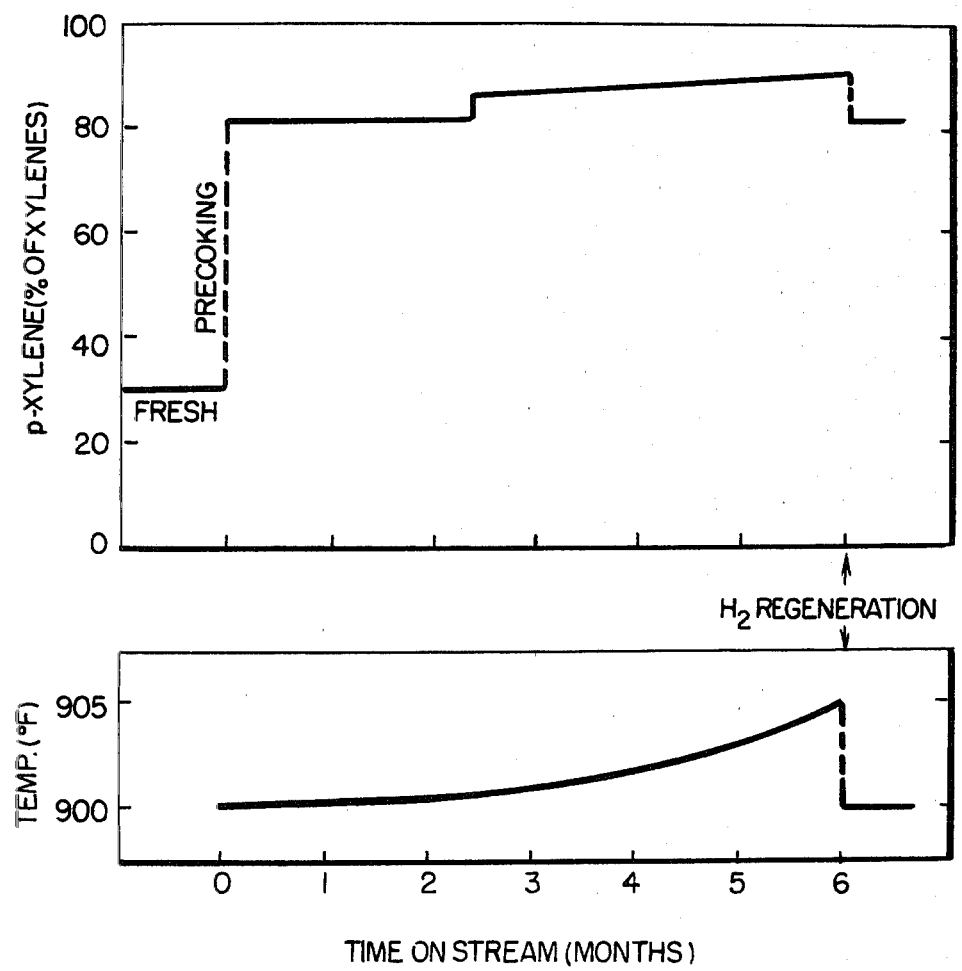
FIG. 2 of the drawing depicts selectivity for para xylene and conversion of toluene with time on stream during disproportionation of toluene over a coke-selectivated crystalline aluminosilicate zeolite catalyst of the type used in the present invention.

The used catalyst of Example 6 was hydrogen regenerated by passing hydrogen thereover at 1000° F. and 400 psig for a total of 68 hours. After this regeneration, the catalyst produced 82 percent para-xylene in total xylenes at 24 percent conversion at a temperature of 900° F., i.e., at the test conditions at the beginning of the catalytic cycle of Example 6. The para-xylene selectivity changes for the catalyst materials of Example 5, 6 and 7 are summarized in FIG. 2.

It is to be understood that the foregoing description is merely illustrative of preferred embodiments of the invention of which many variations may be made by those skilled in the art within the scope of the following claims without departing from the spirit thereof.

What is claimed is:

1. A process for catalytically converting lower monohydric alcohols and corresponding ethers by contacting the same, under catalytic conditions, with a catalyst comprising a crystalline aluminosilicate zeolite characterized by a silica to alumina mole ratio of at least about 12 and a constraint index within the approximate range of 1 to 12, which catalyst has undergone controlled precoking by contact with a thermally decomposable organic compound at a temperature in excess of the decomposition temperature of said compound but less than about 1200° F. at a hydrogen to organic compound mole ratio of between 0 and 1 to deposit at least about 1 weight percent of coke thereon and using the thus precoked catalyst in conversion of said lower monohydric alcohols and corresponding ethers to a hydrocarbon product rich in olefins under conditions of lesser severity which include at least one variable of a lower temperature or a higher hydrogen concentration than employed during the aforesaid precoking with consequent deposition of carbonaceous deposit and loss in conversion activity of said catalyst and thereafter effecting regeneration of the aged catalyst by exposure to an atmosphere comprising hydrogen at a temperature between about 800° F. and about 1200° F. and a pressure between about 0 and about 2000 psig for a period of time sufficient to substantially restore the activity of the catalyst.

2. The method of claim 1 wherein said crystalline aluminosilicate zeolite is ZSM-5.

3. The method of claim 1 wherein the regeneration conditions include a temperature between about 900° and about 1100° F. and a pressure between about 100 and about 1000 psig.

4. The method of claim 1 wherein said period of time is between about 1 and about 48 hours.

5. The method of claim 1 wherein said crystalline aluminosilicate has a crystal size greater than about 0.5 micron.

6. The method of claim 1 wherein said thermally decomposable organic compound is the same monohydric alcohol or corresponding ether reactant being catalytically converted.

7. The method of claim 1 wherein said crystalline aluminosilicate zeolite is admixed with a binder therefor.

8. The method of claim 2 wherein said ZSM-5 is admixed with a binder therefor.

9. The method of claim 8 wherein said binder is alumina.

* * * * *

UNITED STATES PATENT AND TRADEMARK OFFICE
CERTIFICATE OF CORRECTION

PATENT NO. : 4,358,395

DATED : November 9, 1982

INVENTOR(S) : Werner O. Haag et al

It is certified that error appears in the above—identified patent and that said Letters Patent is hereby corrected as shown below:

Column 4, line 14 change "herin" to read --herein--.

Column 8, line 17 insert $--t_{0.3}=F \cdot t_{0.05}--$ after "5% sorption:".

Column 10, line 16 change "exlenes" to --xylenes--.

Signed and Sealed this

Seventeenth Day of May 1983

[SEAL]

Attest:

DONALD J. QUIGG

Attesting Officer — Acting Commissioner of Patents and Trademarks